United States Patent
Puvvada et al.

[11] Patent Number: 5,929,019
[45] Date of Patent: Jul. 27, 1999

[54] CLEANSING COMPOSITION WITH SEPARATELY DISPENSED CLEANSING BASE AND BENEFIT BASE WHEREIN BENEFIT BASE ALSO COMPRISES SURFACTANT

[75] Inventors: Sudhakar Puvvada, Rutherford; May Shana'a, Fort Lee, both of N.J.

[73] Assignee: Lever Brothers Company, Division of Conopco, Inc., New York, N.Y.

[21] Appl. No.: 08/791,127

[22] Filed: Jan. 30, 1997

[51] Int. Cl.$^6$ .................................. C11D 3/16; A61K 7/00
[52] U.S. Cl. ..................... 510/406; 510/120; 510/121; 510/122; 510/130; 510/158; 510/159; 510/404; 510/437; 424/401; 514/844
[58] Field of Search ...................... 510/439, 406, 510/404, 120, 121, 122, 130, 158, 159, 437; 424/401; 514/844

[56] References Cited

U.S. PATENT DOCUMENTS 5,612,307  3/1997  Chambers et al. .................. 510/406

FOREIGN PATENT DOCUMENTS

| 468703 | 1/1992 | European Pat. Off. . |
| 61-215310 | 9/1986 | Japan . |
| 90/13283 | 11/1990 | WIPO . |
| 94/03152 | 2/1994 | WIPO . |

Primary Examiner—Lorna Douyon
Attorney, Agent, or Firm—Ronald A. Koatz

[57] ABSTRACT

An aqueous liquid cleansing and moisturizing composition comprising a base formulation and an additive formulation in which the base formulation and additive formulation are separate but combinedly dispensable from a single packaging means in a predetermined ratio as discrete domains. By adding some surfactant to additive formulation stripe, enhanced lather is obtained. Further, some surfactant is assured, even if there is uneven pumping. Finally, greater consumer control of surfactant of moisturizer levels is afforded.

7 Claims, No Drawings ent stripe).

CLEANSING COMPOSITION WITH SEPARATELY DISPENSED CLEANSING BASE AND BENEFIT BASE WHEREIN BENEFIT BASE ALSO COMPRISES SURFACTANT

FIELD OF THE INVENTION

The present invention relates to detergent compositions suitable for topical application for cleansing and improving the condition of the human body, particularly for moisturizing the skin, hair, nails and other epithelial tissues, including the mucosae. In particular, it relates to compositions which are formulated both to give mild cleansing and to condition the skin.

BACKGROUND OF THE INVENTION

Compositions which both provide a cleansing function and a moisturizing benefit are known. For example, WO 90/13283 discloses compositions comprising acyl ester of an isethionic acid salt, a long chain fatty acid, a moisturizer component and optional soap.

One problem which had been previously encountered with such dual purpose compositions is that they contain an insufficient level of moisturizer component; or an insufficient amount deposits on use.

Another problem associated with such dual cleansing and moisturizing compositions is instability. According to WO 94/03152, concerned with shower gels comprising a non-soap detergent, silicone oil and cationic polymers, the maximum average droplet size of the silicone oil that can be used is 2 microns, if product stability is to be maintained.

In applicants copending U.S. Ser. No. 08/475,145, filed Jun. 7, 1995 and now U.S. Pat. No. 5,612,307, applicants found that enhanced deposition of benefit agent could be obtained in a stable formulation by using a dual cleansing and moisturizing product in which the cleansing and moisturizing components were separately, but combinedly dispensed from a packaging means as discrete domains/stripes.

More specifically, the compositions of that reference comprised a surfactant containing base formulation and a benefit agent wherein the benefit agent and base formulation were physically separate (not in direct contact) but were nonetheless dispensable from a single packaging means comprising both the base formulation and benefit agent as individual stripes. The stripes had width of at least 1000 microns and base formulation and benefit agent stripes were not post mixed prior to use (compared to EP 468,703 to Unilever where post-mixing is required).

The present invention relates to the same separately dispensed, non-mixed prior to use, dual cleanser/moisturizer compositions described in U.S. Ser. No. 475,145 (which reference is hereby incorporated by reference into the subject application) except that the benefit agent stripe has been modified so that it now may include surfactant.

More specifically, U.S. Ser. No. 475,145 suffered from several deficiencies which the present invention overcomes. First, the compositions of that reference, when dual dispensed, did not lather as well as the composition of the subject invention. In addition, if a person were to pump stripes from the dispenser separately, or unevenly, they could end up with a composition containing no surfactant at all. This could not happen in the present invention where both stripes contain at least some surfactant. Finally, by adding surfactant to the benefit agent stripe, the present invention allows the user a greater degree of control over exactly how much cleansing they want (i.e., the benefit agent cleanser having more moisturizer and less cleanser than the primary surfactant-containing stripe).

BRIEF SUMMARY OF THE INVENTION

Suddenly and unexpectedly, applicants have found that, by adding some surfactant to the benefit agent stripes, they can (1) enhance total lather; (2) significantly ameliorate problems associated with inadvertent, uneven striping; and (3) add control to the user as to how much or how little cleanser is dispensed.

More specifically, the present invention comprises an aqueous liquid cleansing and moisturizing composition comprising:

(a) 10 to 99.9% by wt., preferably 30 to 70% by wt. total product of a base formulation comprising 1% to 35% by wt. of base formulation of a surface active agent selected from the group consisting of anionic, nonionic, amphoteric/zwifterionic and cationic surfactants and mixtures thereof; and balance water and other optional ingredients (e.g., cationic polymers, perfumes, thickeners, opacifiers, etc.); and (b) 0.1% to 90% by wt., preferably 30% to 70% by wt. total product of an additive formulation comprising:
  (i) 1% to 80% by wt., preferably 5% to 60% by wt. of the additive composition (i.e., "benefit-containing" formulation) comprising benefit agent;
  (ii) 0.1 to 20% by wt., preferably 5% to 20% by wt. of the additive formulation comprising of a surfactant selected from the group consisting of anionic, nonionic, amphoteric/zwitterionic and cationic surfactants and mixtures thereof; and
  (iii) balance water and optional ingredients (e.g., perfume, thickeners, opacifiers, Cationic Polymers, etc.)

wherein the additive formulation and the base formulation are physically separate such that the formulations are not in direct contact with each other (i.e., are physically separate), but are nonetheless dispensed from a single packaging means comprising both the base and additive formulations as individual stripes;

wherein each stripe comprises either the benefit containing additive formulation or said base formulation;

wherein each stripe has width of at least 1000 microns; and wherein (a) and (b) are not post-mixed prior to use.

DETAILED DESCRIPTION OF THE INVENTION

The present invention relates to aqueous liquid cleansing and moisturizing compositions comprising:

(a) a base formulation comprising a surface active agent selected from the group consisting of anionic (including soap) nonionic, amphoteric/zwitterionic and cationic surface active agents and mixtures thereof; and balance water and optionals; and (b) an additive formulation comprising:
  (i) a benefit agent;
  (ii) additional surfactant; and
  (iii) balance water and optionals;

wherein the additive formulation stripe and base formulation stripe are physically separate but combinedly dispensable from a single packaging means in a predetermined ratio as discrete domains, the domains having one dimension of at least about 1000 microns.

One advantage of the present invention is that it leads to improved lather. While not wishing to be bound by theory, this is believed to be due to lathering effect of surfactant in the additive stripe. A second advantage is the ability to allow the user to obtain cleanser/surfactant from either pump, even if the consumer inadvertently (or purposely) pushed only one side of the pump. Finally, by allowing the consumer to select from two different concentrations of cleanser, the consumer is in much greater control of exactly how much cleanser they wish to use.

The base formulation and additive formulation (comprising benefit agent) are dispensable from a single packaging means in a predetermined ratio according to the use for which composition is intended. An advantage of dispensing the base formulation stripe and additive stripe (containing benefit agent) in combination is that it avoids the inconvenience of having to post mix the two components. This is particularly advantageous when the separate components of a composition need to be mixed in precise ratios in order to achieve the desired effect.

The discrete domains of the composition of the invention may be considered as separate stripes of base formulation and of additive formulation.

The composition is suitable for cleansing and "moisturizing", "conditioning" or "protection" of the skin.

ADDITIVE STRIPE

The benefit agent of the additive stripe is included in the composition to moisturize, condition and/or protect the skin. By "benefit agent" is meant a substance that softens the skin (stratum corneum) and keeps it soft by retarding the decrease of its water content and/or protects the skin.

Preferred benefit agents include:

(a) silicone oils, gums and modifications thereof such as linear and cyclic polydimethylsiloxanes, amino, alkyl alkylaryl and aryl silicone oils;

(b) fats and oils including natural fats and oils such as jojoba, soybean, sunflower, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, petroleum jelly, microcrystalline wax, ceresin, squalene, squalane, and mineral oil;

(f) higher fatty acids such as lauric, myristic, palmitic, stearic, behenic, oleic, linoleic linolenic, lanolic, isostearic and poly unsaturated fatty acids (PUFA) acids;

(g) higher alcohols such as lauryl, cetyl, steryl, oleyl, behenyl, cholesterol and 2-hexadecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate (for example lauryl lactate), alkyl citrate and alkyl tartrate;

(i) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole,eugenol, citral, citronelle, borneol, linalool, geraniol, evening primrose, camphor, thymol, spirantol, pinene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids;

(n) humectants such as glycerin, propylene glycol and sorbitol; and (o) mixtures of any of the foregoing components.

Where adverse interactions between the benefit agent and surface active are likely to be particularly acute, the benefit agent may be incorporated in the compositions of the invention in a carrier.

Such benefit agents include lipids; alkyl lactates; sunscreens; esters such as isopropyl palmitate and isopropyl myristate; and vitamins. The carrier can, for example, be a silicone or hydrocarbon oil which is not solubilized/micellized by the surface active phase and in which the benefit agent is relatively soluble.

Particularly preferred benefit agents include silicone oils, gums and modification thereof, esters such as isopropyl palmitate and myristate and alkyl lactates, and vegetable oils such as sunflower seed oil.

The benefit agent can be provided in the form of an emulsion.

The benefit agent of the invention may also function as a carrier to deliver efficacy agents to skin treated with the compositions of the invention. This route is particularly useful for delivering efficacy agents which are difficult to deposit onto the skin or those which suffer detrimental interactions with other components in the composition. In such cases the carrier is as often a silicone or hydrocarbon oil which is not solubilized/micellized by the surface active phase and in which the efficacy agent is relatively soluble. Examples of such efficacy agents include anti-viral agents; hydroxycaprylic acids; pyrrolidone; carboxylic acids; 3,4, 4'-trichlorocarbanilide; benzoyl peroxide; perfumes; essential oils; germicides and insect repellents such as 2,4,4'-trichloro-2'-hydroxydiphenyl ether (Irgasan DP300); salicylic acid; willow extract, N,N-dimethyl m-toluamide (DEET); and mixtures thereof.

The benefit agent preferably comprises 1 to 80% additive formulation stripe, preferably 5 to 60% of the additive composition.

As seen in the examples, use of surfactant allows greatly improved lathering of the entire composition.

The surface active agent used in the additive stripe can be selected from any known surfactant suitable for topical application to the human body. Mild surfactants, i.e., surfactants which do not damage the stratum corneum, the outer layer of skin, are particularly preferred.

One preferred anionic detergent is fatty acyl isethionate of formula:

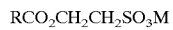

$$RCO_2CH_2CH_2SO_3M$$

where R is an alkyl or alkenyl group of 7 to 21 carbon atoms and M is a solubilizing cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

$$RO(CH_2CH_2O)_nSO_3M$$

where R is an alkyl group of 8 to 22 carbon atoms, n ranges from 0.5 to 10 especially from 1.5 to 8, and M is a solubilizing cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilizing cation.

Sarcosinates are generally indicated by the formula: $R^5CON(CH_3)CH_2CO_2M$, wherein $R^5$ ranges from $C_8$–$C_{20}$ alkyl, preferably $C_{12},C_{15}$ alkyl and M is a solubilizing cation.

Taurates are generally identified by the formula: $R^5CONR^6CH_2CH_2SO_3M$, wherein $R^5$ ranges from $C_8$–$C_{20}$ alkyl, preferably $C_{,2}$–$C_{15}$ $R^6$ ranges from $C_1$–$C_4$ alkyl, and M is a solubilizing cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Suitable surfactants which may be used also include zwitterionic detergents which have an alkyl or alkenyl group of 7 to 18 carbon atoms and comply with an overall structural formula:

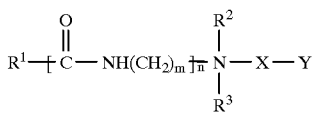

where $R^1$ is alkyl or alkenyl of 7 to 18 carbon atoms $R^2$ and $R^3$ are each independently alkyl, hydroxyalkyl or carboxyalkyl of 1 to 3 carbon atoms;

m is 2 to 4;

n is 0 or 1;

X is alkylene of 1 to 3 carbon atoms optionally substituted with hydroxyl; and

Y is —$CO_2$ or $SO_3$.

Zwitterionic detergents within the above general formula include simple betaines of formula:

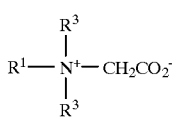

and amido betaines of formula:

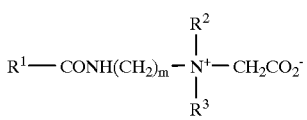

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the group $R^1$ has 10 to 14 carbon atoms. $R^2$ and $R^3$ are preferably methyl.

A further possibility is a sulphobetaine of formula:

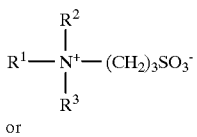

or

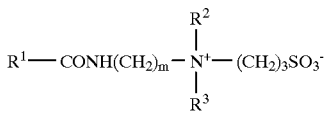

where m is 2 or 3, or variants of these in which $(CH_2)_3SO_3^-$ is replaced by

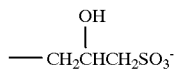

$R^1$, $R^2$ and $R^3$ in these formulae are as defined previously.

Mixtures of any of the foregoing surface active agents may also be used.

The surface active agent is preferably present at a level of from 0.1 to 20 wt. %, preferably 5 to 20 wt % of the additive stripe formulation.

Thickeners may also be added to the additive stripe formulation in order to achieve the required viscosity during use. Preferred thickeners for the benefit agent include fumed silica; polyethylene; alkyl silicone wax; aluminum silicate; lanosterol; natural and synthetic waxes; fatty acids and derivatives thereof, in particular, fatty acid monoglyceride polyglycol ethers; higher fatty alcohols; petrolatum; narogel; polyammonium stearate; hydrotalcites; and mixtures thereof.

Some materials may function as both a benefit agent and a thickener. For example, it will be understood that where the composition comprises two or more benefit agents, one of said benefit agents may also function as a thickening agent.

Further examples of structurants and thickeners are given in the International Cosmetic Ingredient Dictionary, Fifth Edition, 1993, published by CTFA (The Cosmetic, Toiletry & Fragrance Association), incorporated herein by reference.

The balance of additive stripe will comprise water and optionals such as perfumes, opacifiers, cationic polymers etc.

BASE FORMULATION STRIPE

The "base" formulation stripe may include any of the surfactants (or mixture of surfactants) described for use in the "additive" stripe formulation discussed above.

In addition a structurant may be added to the base formulation composition. Suitable materials include swelling clays, for example laponite; fatty acids and derivatives thereof, in particular, fatty acid monoglyceride polyglycol ethers; cross-linked polyacrylates such as Carbopol (™) (polymers available from Goodrich); acrylates and copolymers thereof; polyvinylpyrrolidone and copolymers thereof; polyethyleneimines; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The base formulation may also comprise a thickening (or thinning) agent, i.e., a material which maintains the viscosity of this phase as the shear rate thereof is increased during use. Suitable materials include cross-linked polyacrylates such as Carbopol (™) (polymers available from Goodrich); natural gums including alginates, guar, xanthan and polysaccharide derivatives including carboxy methyl cellulose and hydroxypropyl guar; propylene glycols and propylene glycol oleates; salts such as sodium chloride and ammonium sulphate; glycerol tallowates; and mixtures thereof.

Other typical components of such compositions include opacifiers, preferably 0.2 to 2.0 wt. %; preservatives, preferably 0.2 to 2.0 wt. %; and perfumes, preferably 0.5 to 2.0 wt. %. Cationic polymers such as Jaguar® from Rhone Poulenc and Polymer JR® from Amerchol may also be included.

It is an essential feature of the invention that the additive formulation and base formulation are physically separate but combinedly dispensable from a packaging means and typically a single packaging means. Such a packaging means includes those systems which comprise two separate compartments. Ensuring that the base formulation and additive formulation are separate can be achieved in a variety of ways: Packaging of the composition such that the base formulation and additive formulation are present in separate compartments or in separate domains within the packaging; including encapsulation of the additive formulation; and by processing of the composition by coextrusion to produce a striped product in which individual stripes contain either the base formulation or additive formulation.

Compositions of the invention may be formulated as products for washing the skin, for example, bath or shower gels, hand washing compositions or facial washing liquids; pre- and post-shaving products; rinse-off, wipe-off and leave-on skin care products; products for washing the hair and for dental use.

The compositions of the invention will generally be pourable liquids or semi-liquids e.g., pastes and will have a viscosity in the range 250 to 100,000 mPas measured at a shear rate $10s^{-1}$ and 25° C., in a Haake Rotoviscometer RV20.

When the product is formulated as a shower gel, the viscosity will generally be in the range 800 to 30,000 mPas measured at a shear rate $10s^{-1}$ and 25° C.

When the product is formulated as a facial wash product the viscosity will generally be in the range 3000 to 100,000 mPas measured at a shear rate $10s^{-1}$ and 25° C.

Except in the operating and comparative examples or otherwise where explicitly indicated, all numbers in this description indicating amounts of materials or conditions of reaction and/or use are to be understood as modified by the word "about".

The invention will be further illustrated by reference to the following non-limiting examples. The examples are for illustrative purposes only and are not meant to limit the claims in any way.

Examples

Lather is measured using the cylinder shaking method. Using this method, 4 g of product having different ratios of surfactant to benefit stripes were dispensed to the bottom of a 250 ml graduated cylinder; 50 g of water was then gently added; and the cylinder was capped and then gently shaken by turning the cylinder upside down 10 times. The foam volume was then measured.

A liquid cleanser composition was prepared wherein the surfactant stripe had the composition set forth in Table I and the benefit stripe had the composition set forth in either Example 1 or in the comparative in Table II (Example 1 having 10% by wt. benefit stripe surfactants and comparative having no surfactant). Table I and II are set forth below:

Surfactant Stripe

TABLE 1

| Ingredients | % by wt. |
| --- | --- |
| Amphoteric (e.g., cocoamidopropyl betaine) | 15–20% |
| Anionic surfactant (e.g., sodium laureth sulfate) | 10–15% |
| Humectants (e.g., glycerin) | 1–3% |
| Cationic polymers (e.g., polyquaternium) | 0.1–1.0% |
| Nonionic (e.g., PEG 80 Sorbitan monolaurate) | 1–3% |
| Sodium Hydroxide | 0.11 |
| Opacifier (e.g., styrene acrylate) | 0.4 |
| Preservative (e.g., DMDM hydantoin) | 0.2 |
| Fragrance | 1.0 |
| Water | to 100.0 |

Benefit Stripe Examples

TABLE II

| Ingredients | % by wt. Example 1 | % by wt. Comparative |
| --- | --- | --- |
| Amphoteric surfactant (e.g., sodium lauroamphoacetate) | 6 | 0 |
| Anionic surfactant (e.g., sodium laureth sulfate) | 4 | 0 |
| Sunflower seed oil | 40% | 40% |
| Humectant (e.g., glycerin) | 3–7% | 3–7% |
| Guar hydroxypropyl-trimonium chloride | 1 | 1 |
| PEG 80 Sorbitan monolaurate | 2 | 2 |
| Palm kernel acid | 2.6 | 2.6 |
| Citric acid | 0.5 | 0.5 |
| Magnesium sulfate | 0.5 | 0.5 |
| DMDM Hydantoin | 0.2 | 0.2 |
| Fragrance | 1.0 | 1.0 |
| Water | to 100.0 | to 100.0 |

Using the lather measurement technique described above, different of 4 grams of surfactant stripe and benefit stripe were dispersed and measurements of foam were taken. The results are set forth in Table III below:

TABLE III

| Surfactant Stripe (grams) | Benefit Stripe (grams) | Foam Volumes (ml) | |
|---|---|---|---|
| | | Benefit Stripe with surfactants Example I | Benefit Stripe w/o surfactants Comparative |
| 0 | 4 | 105:5 | 10 |
| 0.4 | 3.6 | 101 | 18 |
| 1.2 | 2.8 | 94 | 23 |
| 2.0 | 2.0 | 99 | 58 |
| 2.8 | 1.2 | 96 | 93 |
| 3.6 | 0.4 | 88 | 89 |
| 4 | 0 | 128 | 128 |

As can be clearly seen from Table III above, when surfactant is used in the benefit stripe (Example I), there is much greater consistency in the amount of lather delivered no matter how the stripes are dispensed. By contrast, when no surfactant is present (Comparative), foaming is high only when more of this surfactant stripe is dispensed. Inadvertently dispensing of greater amounts of benefit stripe clearly results in poor lathering. Even at 50–50 distribution, lather is much higher when surfactant is based in benefit stripe (99 ml) then if there were no surfactant in benefit stripe (58 ml).

Example 2

In this example, applicants used the same surfactant stripe as in Example 1 and benefit stripe used slightly different composition as set forth in Table IV below.

Benefit Stripe Examples

TABLE IV

| Ingredients | Example 2 | Comparative 2 |
|---|---|---|
| Cocoamido propyl betaine | 4 | 0 |
| Anionic surfactant (e.g., sodium cocoyl isethionate) | 6 | 0 |
| Petrolatum | 30 | 30 |
| Propylene glycol | 2 | 2 |
| Guar hydroxypropyl-trimonium chloride | 0.5 | 0.5 |
| DMDM Hydantoin | 0.2 | 0.2 |
| Fragrance | 1.0 | 1.0 |
| Water | to 100.0 | to 100.0 |

All amount are in % by weight.

Again, Comparative 2 has no surfactant.

Using the lather measurement test described above, foam values were measured and results set forth in Table V below:

TABLE V

| Surfactant Stripe (grams) | Benefit Stripe (grams) | Foam Volumes (ml) | |
|---|---|---|---|
| | | Benefit Stripe with surfactants (Example 2) | Benefit Stripe w/o surfactants (Comparative) |
| 0 | 4 | 142 | 0 |
| 0.4 | 3.6 | 166 | 72 |
| 1.2 | 2.8 | 179 | 131 |
| 2.0 | 2.0 | 176 | 146 |
| 2.8 | 1.2 | 174 | 158 |

TABLE V-continued

| Surfactant Stripe (grams) | Benefit Stripe (grams) | Foam Volumes (ml) | |
|---|---|---|---|
| | | Benefit Stripe with surfactants (Example 2) | Benefit Stripe w/o surfactants (Comparative) |
| 3.6 | 0.4 | 152 | 172 |
| 4 | 0 | 169 | 169 |

Again, results clearly demonstrate that lather volume is far more consistent, no matter how the stripes are dispensed (e.g., even at 0 grams surfactant stripe and 4 grams benefit agent stripe) when the benefit agent stripe contains surfactant.

We claim:

1. Aqueous liquid and moisturizing composition comprising:
   (a) 10% to 99.9% by wt. total product of a base composition comprising 1 to 35% by wt. base composition of a surface active agent selected from the group consisting of anionic, nonionic, amphoteric/zwitterionic and cationic surfactant and mixtures thereof; and balance water; and
   (b) 0.1% to 90% by wt. total product of an additive composition comprising:
      (i) 5 to 80% by wt. of additive composition of a benefit agent;
      (ii) 0.1% to 20% by wt. of additive composition of a surfactant selected from the group consisting of anionic, nonionic, amphoteric/zwitterionic and cationic surfactants and mixtures thereof wherein at least an anionic surfactant and at least an amphoteric/zwitterionic surfactant are present inn said additive composition; and
      (iii) balance water;
   wherein additive composition and base composition are physically separate, but are dispensed from a single packaging means comprising both the base and additive compositions as individual stripes;
   wherein each stripe comprises either the benefit containing additive composition or said base composition;
   wherein each stripe has a width of at least 1000 microns;
   wherein (a) and (b) are not post mixed prior to use; and
   wherein the foam height of benefit agent stripe is greater than about 88 ml using the cylinder shaking method.

2. A composition according to claim 1, wherein component (a) is 30 to 70% by wt. total product.

3. A composition according to claim 1, wherein said base composition additionally comprises an optional ingredient selected from the group consisting of cationic polymers, perfumes, thickeners and opacifiers.

4. A composition according to claim 1, wherein component (b) is 30 to 70% by weight total product.

5. A composition according to claim 1, wherein benefit agent is 5 to 60% by weight of additive composition.

6. A composition according to claim 1, wherein surfactant is 5 to 20% by weight of additive composition.

7. A composition according to claim 1, wherein said additive composition additionally comprises an optional ingredient selected from the group consisting of cationic polymer, thickeners, perfumes and opacifiers.

* * * * *